US008777851B2

(12) United States Patent
Alt (10) Patent No.: US 8,777,851 B2
(45) Date of Patent: Jul. 15, 2014

(54) CONGESTIVE HEART FAILURE MONITOR AND VENTILATION MEASURING IMPLANT (75) Inventor: Eckhard Alt, Munich (DE)

(73) Assignee: Medtronic, Inc., Minneapolis, MN (US)

(*) Notice: Subject to any disclaimer, the term of this patent is extended or adjusted under 35 U.S.C. 154(b) by 787 days.

(21) Appl. No.: 10/622,184

(22) Filed: Jul. 16, 2003

(65) Prior Publication Data

US 2004/0116819 A1 Jun. 17, 2004

Related U.S. Application Data (63) Continuation-in-part of application No. 10/155,771, filed on May 25, 2002, now Pat. No. 6,829,503.

(51) Int. Cl.
*A61B 5/00* (2006.01)
*A61B 5/05* (2006.01)
*A61B 5/04* (2006.01)
*A61B 5/053* (2006.01)
*A61N 1/362* (2006.01)
*A61N 1/365* (2006.01)

(52) U.S. Cl.
CPC ........... *A61B 5/0031* (2013.01); *A61B 5/04012* (2013.01); *A61B 5/0537* (2013.01); *A61B 2562/0219* (2013.01); *A61N 1/3622* (2013.01); *A61N 1/36521* (2013.01)
USPC ........................... 600/301; 600/547; 600/509

(58) Field of Classification Search
CPC ............. A61B 5/0031; A61B 5/04012; A61B 5/0537; A61B 2562/0219; A61N 1/3622; A61N 1/36521
USPC ......... 600/547, 518, 508, 481, 513, 529, 301; 607/18, 20, 24, 9
See application file for complete search history.

(56) References Cited

U.S. PATENT DOCUMENTS

| | | | | | |
|---|---|---|---|---|---|
| 4,884,576 | A | * | 12/1989 | Alt | 607/18 |
| 5,876,353 | A | * | 3/1999 | Riff | 600/547 |
| 5,957,861 | A | * | 9/1999 | Combs et al. | 600/547 |
| 6,336,903 | B1 | * | 1/2002 | Bardy | 600/508 |
| 6,600,949 | B1 | * | 7/2003 | Turcott | 600/518 |
| 6,829,503 | B2 | * | 12/2004 | Alt | 600/547 |

* cited by examiner

Primary Examiner — Brian Szmal
(74) Attorney, Agent, or Firm — IPLM Group, P.A.

(57) ABSTRACT

An implanted device-implemented method of detecting and monitoring congestive heart failure in a patient includes performing ongoing measurements of changes in local impedance of a portion of the patient's body between at least two electrodes on the exterior of the implanted device, the changes representing ventilation of the patient, and including measuring the patient's respiratory rate and respiratory amplitude. A body-implantable device is adapted to detect and monitor congestive heart failure in a patient, and includes a circuit module coupled to plural surface electrodes of the device arranged and adapted, when the device is implanted, for contacting tissue in a portion of the patient's body generally occupied by the lungs, to monitor changes in local impedance of said body portion, and to detect the patient's EKG.

3 Claims, 5 Drawing Sheets

CONGESTIVE HEART FAILURE MONITOR AND VENTILATION MEASURING IMPLANT

CROSS-REFERENCE TO RELATED APPLICATION

This application is a continuation-in-part of U.S. patent application Ser. No. 10/155,771, filed May 25, 2002 now U.S. Pat. No. 6,829,503 ("the '771 application"), of the same inventor.

BACKGROUND OF THE INVENTION

The present invention relates generally to implantable medical devices, and more particularly to an implantable device for detecting and monitoring the progression of congestive heart failure.

Many patients who have suffered one or more myocardial infarctions subsequently require treatment for congestive heart failure (CHF). The left heart fails while the pumping function of the right heart remains adequate, because the latter has only about 20% of the workload of the former. This leads to an increase in blood volume congested to the lungs, resulting in pulmonary congestion, build up of edema, and congestion of internal organs including the stomach and intestines. Increased fluid in the stomach and intestines reduce their ability to absorb drugs prescribed for treatment of CHF, particularly diuretics. The congestion is often accompanied by a worsening of myocardial function, with consequent drop in blood pressure and reduced renal perfusion, which only further aggravates the congestive situation. Thus, late recognition of congestion leads to increased dosages of oral diuretics that are unsuccessful to treat the condition, ultimately requiring that the patient be hospitalized.

Avoidance of hospitalization and the pitfalls of late treatment require detection of CHF at an early stage, so that the prescribed drugs can be fully absorbed and effective. If detected early, a combination of diuretics and other drugs can slow the progress of the disease and allow the patient to enjoy an improved lifestyle.

The implantable medical device of the '771 application is of a size smaller than a typical pacemaker device—about the size of a thumb. It is implanted in a subcutaneous pocket in the patient's chest, under local anesthesia and minimally invasive requirements. The device includes a hermetically sealed can with appropriate electronic circuitry inside. A set of can-mounted electrodes is used to measure the impedance of the adjacent tissue and most especially the lung tissue. The progressive retention of fluid in the lungs and congestion of the ventricle together result in a reduced impedance measurement that is monitored either continuously or periodically by the device.

In a preferred mode of operation, the device disclosed in the '771 application alerts the patient and the attending physician when a diagnostic threshold is reached which is indicative of the progression of CHF. The overall architecture of the device follows implantables practice, and is a stand-alone monitoring device. However, the partitioning of the device is flexible and the division of sensing and analysis structures can be shared between implanted and external (remote, i.e., non-implanted) devices. Conventional programming and telemetry links can be used to connect the implanted device to the remote device. For example, the signal processing may be performed entirely internally within the device, or the device may operate as a data logger and communicate with an external programmer device which participates in data reduction and analysis.

It is a principal aim of the present invention to provide an implantable heart failure monitor and ventilation measuring implant that constitutes an improvement over the device of the '771 application, capable of better quantifying and detecting the status of the patient, and especially of achieving very early detection of CHF.

Past attempts made to quantify and detect the cardio-pulmonary status of the patient include the following. U.S. Pat. No. 5,003,976 to Alt discloses a technique to access the cardio-pulmonary status of the patient more accurately from a single sensor located within the heart. U.S. Pat. No. 5,331,966 to Bennett et al. discloses a subcutaneous implant that measures the electrical cardiac signal detected in the body upon depolarization of the heart, using electrical contacts. Tachycardia from the far field electrocardiogram can be recorded to measure capture detection, and a threshold adaptation can be used to save energy when the device is implanted or to provide timing windows for anti-tachycardia pacing therapy, and a control signal for use in adjusting pacing rate to physiologic demand. These techniques utilize intrinsic signals that derive from the patient's own heart beat.

U.S. Pat. No. 5,876,353 to Riff discloses a method to measure edema by evaluating the patient's respiration rate. According to the patent, the respiratory rate of the patient can be detected from a subcutaneous location, and increases with increasing congestion. A subcutaneous implant used for that purpose has an electrode that connects the implant to location within the heart. However, the patent does not indicate a technique to measure ventilation, which is the product of tidal volume and respiratory rate.

U.S. Pat. No. 5,957,861 to Combs et al discloses a monitor together with a pacemaker to detect the occurrence of edema by monitoring a DC (direct current, or base) value. According to the patent, respiratory events are noise that should be filtered out. The disclosed device measures impedance both locally, from electrodes on the device, and from electrodes implanted in the patient's heart. Local impedance measurement is described in the patent as a local edema indicator, not as representing lung edema, but rather with an assumption that lung edema is represented by a transthoracic measurement. The local edema is compared to changes in the transthoracic value to reflect pulmonary, edema. The determinations are based upon comparison of the short term and long term averages, and the discrimination from local edema compares the changes in the local pocket edema to the changes in the transthoracic edema. Signals produced by activity or breathing are excluded from the analysis so to find the DC signal level; all other values are deemed to be noise components.

U.S. Pat. No. 5,987,352 to Klein et al. discloses a minimally invasive implant and a preferred method for detecting physiologic events, by storing the intrinsic heartbeat of the patient—the EKG (electrocardiogram) signals. The EKG signal and additional sensor data may be communicated through telemetry such as used for pacemakers and other implant devices. An elliptical or rectangular shape of less than ½-inch diameter is disclosed.

U.S. Pat. No. 6,190,324 to Klieval, et al. discloses an implantable medical device for tracking patient cardiac status. This disclosure, which is incorporated herein by reference in its entirety, compares heart rate and activity level of the patient, detected from a mechanical electrical converter such as an accelerometer, to derive a quotient of heart rate and activity that is indicative of the patient's cardio-pulmonary status. Other rate signals, such as respiratory rate, may be used as an alternative to the patient's activity level to develop the heart rate activity coefficient. Such an implant is projected to be used in patients with a normal heart rate response, in which a comparison of information from heart rate to the amount of activity would allow a determination of the patient's cardio-pulmonary status.

U.S. Pat. No. 6,512,949 to Combs et al discloses an impedance monitor that detects by DC measurements the amount of edema and additionally works in conjunction with a loop recorder, pacemaker, or defibrillator. The patent further discloses that respiration methods signals are considered to be noise, and are filtered out to obtain the DC value.

SUMMARY OF THE INVENTION

The present invention stems from the recognition that specific structures of the device of the '771 applications that are disclosed as being dedicated to specific tasks, may share functions if the device is integrated with other diagnostic or therapeutic devices. For example, the electrodes that are used to determine the impedance of the lungs may be used for additional purposes, such as to measure EKG and to provide information in addition to the impedance. Further, this EKG information can be stored and evaluated in a loop recorder that record trends of bradycardia and tachycardia, and provides templates and rate information. A mechano-electrical converter, e.g., accelerometer or piezoelectric crystal of the device provides an indication of patient activity. These parameters, together with the detected local impedance information, are utilized to evaluate the cardio-pulmonary status of the patient.

According to one aspect, the invention comprises an implanted device-implemented method of detecting and monitoring congestive heart failure in a patient, including performing ongoing measurements of changes in local impedance of a portion of the patient's body between at least two electrodes on the exterior of the implanted device generally occupied by the lungs, the changes representing ventilation of the patient. The ongoing measurements include measuring the patient's respiratory rate and respiratory amplitude. The method includes controlling the rate of a rate adaptive cardiac pacemaker using the patient's ventilation represented by the measured changes in local impedance. In essence, the rate adaptive pacemaker is equipped with electronic signal processing indicative of absolute respiration rate in breaths per minute and a relative tidal volume signal amplitude with increasing ventilation depth. The method also includes detecting the cardio-pulmonary status of the patient, using the patient's ventilation represented by the measured changes in local impedance. Further included is deriving a signal from the measured changes in local impedance that reflects congestion in heart failure patients. Additionally, the method involves deriving both the patient's ventilation and DC impedance from the measured changes in local impedance, from which to detect an early stage of lung congestion of the patient.

According to another aspect, the invention constitutes a method of early detection of pulmonary congestion in a patient, comprising subcutaneously implanting an impedance monitoring device at a location on the patient's thorax at the lower part of the lungs constituting a site where initial accumulation of fluid occurs in the lungs, and monitoring impedance changes at said location to detect pulmonary congestion. Stated differently, the method involves implanting a subcutaneous impedance measuring device with electrodes connected thereto, and positioning the electrodes to measure impedance on the lower side of the patient's lungs.

Yet another aspect of the invention is a method of monitoring the cardio-pulmonary status of a patient, including detecting the patient's intrinsic heart activity, analyzing and storing the analysis of the detected intrinsic heart activity, evaluating a pattern of the patient's intrinsic heart activity derived from the analysis, and measuring and evaluating impedance at a selected site on the patient's body, and using the impedance evaluation together with the intrinsic heart activity pattern evaluation to derive information representing cardio-pulmonary status of the patient.

A device according to the invention is adapted be implanted subcutaneously to detect and monitor congestive heart failure in a patient, and includes a circuit module coupled to plural surface electrodes of the device arranged and adapted, when the device is implanted, for contacting tissue in a portion of the patient's body generally occupied by the lungs, to monitor changes in local impedance of the body portion, and to detect the patient's EKG. The circuit module utilizes at least two of the electrodes to both monitor said changes in local impedance and detect the patient's EKG. The device also includes an accelerometer to detect physical activity of the patient. A patient alert function and telemetry communication with one or more control units external to the patient's body are also provided for the device.

A feature of the invention is the provision of a body-implantable device that comprises apparatus for measuring a patient's subcutaneous impedance at a location on the patient's body where the measured impedance has a linear correlation with the patient's cardiac output, and for monitoring a decrease in impedance baseline value to indicate cardio-pulmonary status of the patient.

The device of the invention may be characterized as including several subsystems, a first subsystem to detect the patient's intrinsic heart activity, a second subsystem to analyze and store the intrinsic heart activity, a third subsystem to evaluate a physical activity pattern of the patient generated by a mechanical-electrical converter, a fourth subsystem to analyze and store the physical activity pattern, a fifth subsystem to measure and evaluate impedance at a local implant site of the device, and a sixth subsystem to analyze and store the measured impedance, and to derive from the functions of the first, second, third, fourth, fifth and sixth subsystems information representing the cardio-pulmonary status of the patient.

In yet another formulation, the invention constitutes a medical device adapted for subcutaneous implant in a patient to evaluate cardio-pulmonary status of the patient, and includes detection apparatus responsive to the heart rate/activity pattern of the patient and the impedance between a pair of electrodes contacting subcutaneous tissue at opposite sides of a lung of the patient, for performing said evaluation, and evaluation apparatus for evaluating the trend of the heart rate/activity pattern and the impedance against one another, over a selected period of time.

The implantable device includes a housing having electrodes on a surface that constitute the only electrodes of the device, to be used for detecting local impedance changes therebetween and a locally derived EKG after implantation. The housing also incorporates a mechano-electrical converting element, such as an accelerometer, for responding to the status of physical activity of the patient. An electronic module in the housing uses information derived from the impedance changes, the EKG and the status of physical activity, to determine the status of congestive heart failure of the patient, as well as the need for increasing or decreasing the heart rate of the patient, and also the occurrence of potentially lethal arrhythmias of the patient.

The invention also pertains, to an improvement in implantable rate adaptive cardiac pacemakers, in which electrodes are situated on one of the housing and the header of the pacemaker, and an electronic module in the housing measures impedance changes at the electrodes when the pacemaker is implanted, to control the pacing rate generated by the pacemaker. An accelerometer in the pacemaker detects the status of physical activity of the patient, to assist in controlling the pacing rate of the pacemaker.

BRIEF DESCRIPTION OF THE DRAWINGS

The above and other aims, objectives, aspects, features and attendant advantages of the invention will be further understood from a reading of the following detailed description of the best mode presently contemplated for practicing the invention, taken with reference to certain presently preferred embodiments and methods, and in conjunction with the accompanying drawings, in which.

DETAILED DESCRIPTION OF THE PRESENTLY CONTEMPLATED BEST MODE OF PRACTICING THE INVENTION

The description of the device and methods of the present invention is aided by reference to the structure and operation of diagnostic device of the '771, application, illustrated in FIGS. 1-5, and summarized below. Throughout the several views of the drawings, identical reference numerals indicate identical structure. Views of the prior device or the device of the present invention, either alone or as implanted, are not intended to represent actual or relative sizes.

Figure 1:
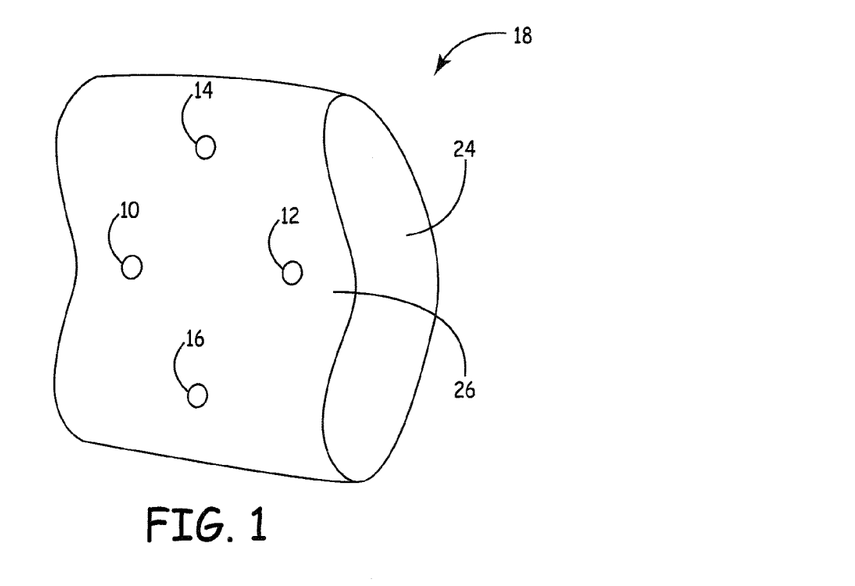
FIG. 1 is an exterior view of an embodiment of the device of the '771 application.

FIG. 1 illustrates the exterior of device 18, which includes a circuit module (discussed below in conjunction with the description of FIG. 3) within a hermetically sealed "can" or case 24 composed, for example, of titanium. The size of the case 24 is dictated by the size of the internal circuit components and wiring included printed circuit board(s) and other forms, but preferably is very small, e.g., about 5.0 cm. long by 2.0 cm wide by less than 1.0 cm thick.

Case 24 has a curvilinear shape that presents a concave shape or surface 26 on one side (in contrast to an edge of the case) and a convex shape on the opposite side of the case. Four surface mounted electrodes 10, 12, 14 and 16 are positioned in spaced-apart relationship on the slightly concave surface 26, each electrode being electrically insulated from the case 24 itself. The electrodes are of low polarization, and may be composed of or coated with iridium oxide. For example, "inner" electrodes 10 and 12 are spaced apart on the concave side inward of opposite edges and centrally along the length of the case, while "outer" electrodes 14 and 16 are spaced further apart—e.g., at least about 4 cm—on that same side inward of opposite edges and centrally along the width of the case. The shape of the case is designed to conform to the shape of the anatomy of the human chest at the location where the device is to be subcutaneously implanted. With the concave side of the case placed toward the interior of the body within the implant site of device 18, the device is prevented from turning within its subcutaneous pocket.

Figure 2:
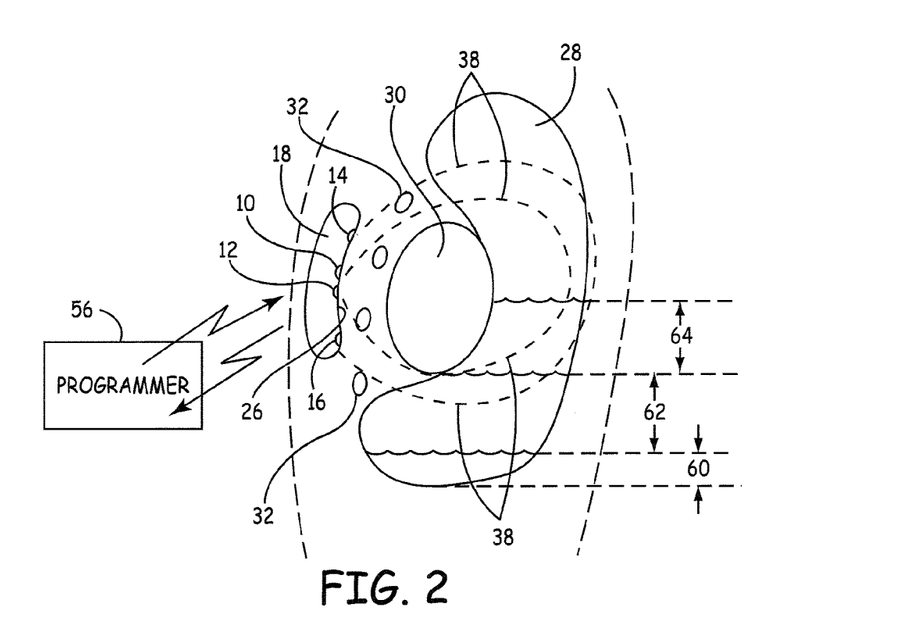
FIG. 2 is a schematic representation of an implantation of the device of FIG. 1 in the body of a patient.

A preferred implant site of the device is the left lower anterior lateral hemithorax of the patient's body as shown in FIG. 2. In part, this is because optimal sensing occurs with the device placed slightly to the left of the patient's midline. Preferably, an external optimization process is conducted before implantation, to determine the individual optimum position of the device for detecting the respective EKG signal and the impedance, since the optimum site for this purpose may vary from patient to patient. FIG. 2 illustrates in schematic form a side view of a patient (in phantom) with the device 18 implanted in a pectoral of the chest over the basal region of lungs 28 and heart 30, outside the rib cage 32. An implantation at the preferred, site places the device on the left anterior thorax side between the 5th and 6th intercostals space. In this position of the device, an impedance signal is developed which represents the impedance of the lungs and heart tissue by virtue of current injected into the circuit path that establishes a field through that portion of the body from device 18.

Figure 3:
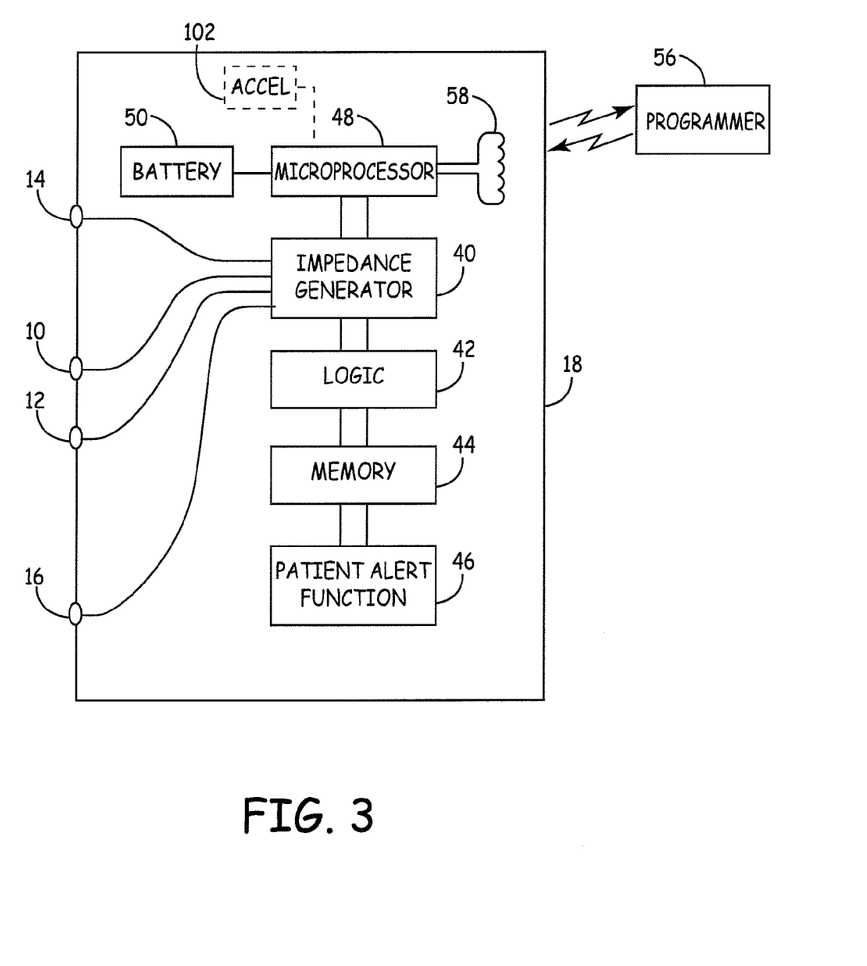
FIG. 3 is a block diagram of the internal circuitry of the device of FIG. 1.

FIG. 3 illustrates the circuit module within device 18. An impedance signal generator 40 injects signal current into the body, preferably through "inner" electrodes 10 and 12. The current traverses the circuit path through the body portion of interest and has a return path through "outer" electrodes 14 and 16. Field lines 38 (FIG. 2) attributable to current flowing from the electrodes emanate from the concave side 26 of device 18, and, together with the electrode spacing, define the "viewing volume" of the device for the impedance sensing circuitry. Electrode spacing of at least four cm between the outer electrodes 14, 16 will allow a measurement to a depth of up to 10 cm of lung tissue in the anterior lateral lower left thorax. The field lines produced by current through the circuit path intersect the lung tissue 28 and are somewhat less influenced by the volume of the heart 30.

The circuit module within device 18 is powered by a preferably lithium-ion battery 50. Impedance generator 40 is controlled by microprocessor 48, as is logic 42 for analysis and memory 44 for data. Measured values of impedance are stored in memory 44, and used by microprocessor 48 to calculate long-term and short-term averages of the measured impedance values. A threshold detector 46 may be incorporated in device 18 as a patient alert function or alarm (e.g., by emitting an acoustic signal, vibrations, or low level pulses for local muscle contractions, recognizable by the patient) indicative of a need for immediate intervention when a condition associated with fluid level congestion 64, for example, is detected. Such an alarm condition may also be signaled by telemetry from an antenna or coil 58 within the circuit module at the microprocessor, normally used to transmit the other impedance data, to a remote programmer 56 to monitor and log the progress of the disease and the therapeutic effect of treatment for review by the patient's physician.

The device is adapted to monitor impedance at a digital rate of 128 Hz, for partitioned analysis of contractile cardiac function, pulmonary ventilation function and long term pulmonary impedance, over an average of 72 hours or more. Signal processing, allows deviation from basic impedance of the body region of interest, especially the lungs, to be detected as an early monitoring of a decrease in lung impedance, indicative of increasing congestion by fluid content in the lungs. The decrease in lung impedance associated with CHF occurs as the lungs fill with fluid, which is a considerably better electrical conductor than the normal lung tissue. Exemplary values of impedance for lung tissue are 400 to 1,000 ohms per centimeter (Ω/cm), compared to about 50 Ω/cm for fluid.

Representative fluid levels accumulated in the lungs are illustrated in FIG. 2 at 60, 62 and 64. Level 60 represents the relative additional amount of fluid associated with normal lung function. Level 62 represents the relative amount of fluid present for a compromised lung function associated with CHF. And level 64 is the relative still additional amount of fluid associated with severely reduced lung function requiring immediate attention, indicative of advanced CHF.

The device 18 may be designed to provide a threshold or trigger level at an accumulation of fluid corresponding approximately to level 64. Algorithms are used to convert real time measurements into a diagnostic indication of congestion. The device may be operated continuously and the impedance data are then analyzed in kind. EKG data may be (and is, in the improved device of the present invention) used additionally, detected at the outer electrodes 14 and 16 to improve the capability of the device to discern impedance changes in the heart. In particular, the occurrence of tachyarrhythmias is often indicative of a worsening left ventricular function. Tachyarrhythmias consisting of runs of fast ventricular beats are precursors of fatal arrhythmias such as sustained ventricular tachycardias and ventricular fibrillation. The occurrence of these marker arrythmias as well as pathologic slow heart rates is monitored and triggers a patient alert warning.

Figure 4:
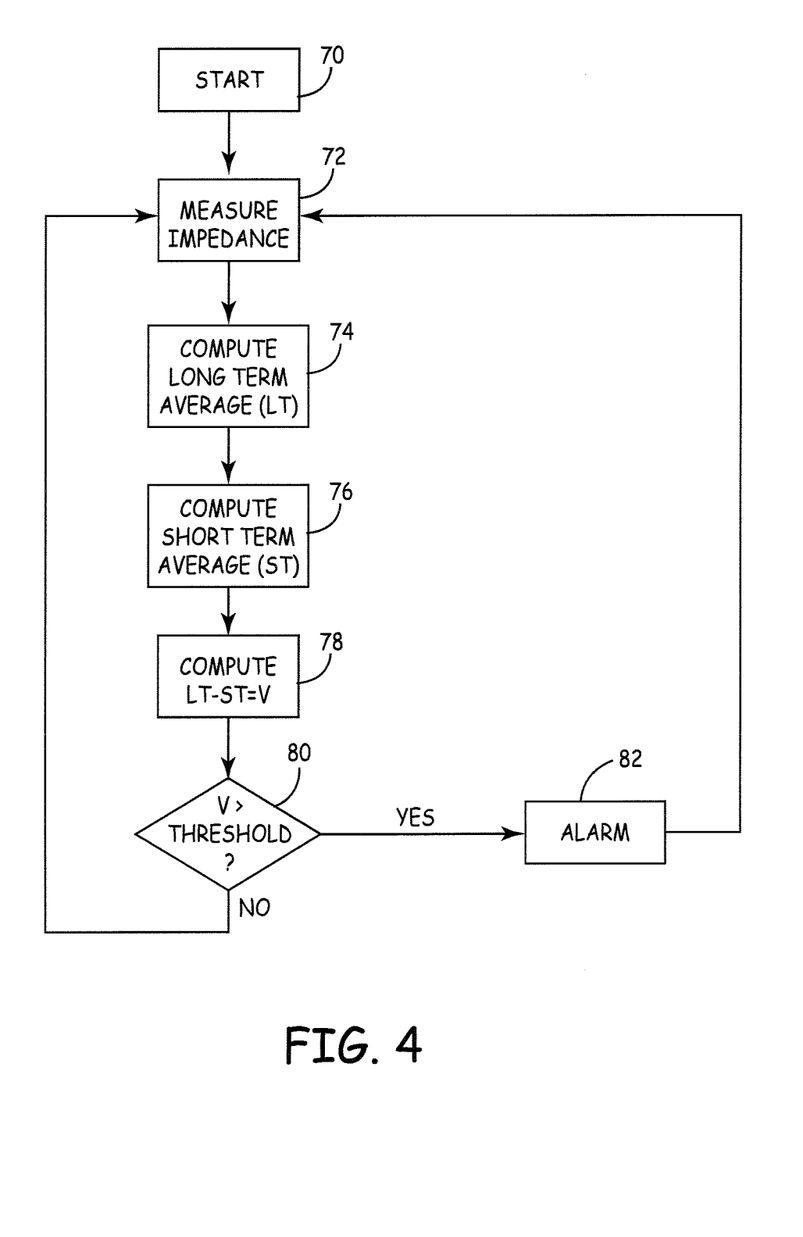
FIG. 4 is a flow chart illustrating the operation of the device of FIG. 1.

FIG. 4 is a flow chart of an exemplary detection algorithm used by the device 18. On commencement, counters are initialized and impedance generator 40 is turned on to inject signal current into the body via the inner pair of electrodes 10, 12 (start, 70). The impedance signal current is preferably a rectangular biphasic pulse wave at a rate of 128 Hz and a peak-to-peak amplitude of 1 milliampere (ma), or, alternatively, an alternating current in a range from 5 microamperes (µa) to 10 µa. The pulses may be injected with considerably higher energy content than the AC wave because of their very short duration (e.g., 15 µsec or less), with no risk of myocardial depolarization, and are capable of detecting cardiac changes as well as pulmonary changes.

Impedance is then calculated (72) from a measurement of the resulting voltage at the outer pair of electrodes 14, 16. Alternatively, a fixed voltage may be applied across the excitation (inner) electrodes and the resulting current measured at the measurement (outer) electrodes reflects the impedance. A longterm average of the impedance value is computed (74), covering a period ranging from days to weeks as a running average. A short-term average of the impedance value is also computed (76), covering a period from hours to days. The difference between the long-term (LT) and short-term (ST) averages is calculated (78) as a slope measurement (V) indicative of deterioration of the lung condition, to detect accelerating lung congestion. If the value V exceeds a predetermined threshold (slope) value (80), an alarm condition is indicated and the patient alert function (46, FIG. 3) is initiated. In either case (an alarm condition or not), another impedance measurement is performed (72) and the processing cycle is repeated.

As described above in conjunction with FIG. 2, detection of lung congestion requiring immediate attention is obtained from a simple volume measurement, but a slope measurement may be preferable to determine when an alarm condition is occurring or has occurred, because the variability of impedance signals makes it more difficult to achieve accurate threshold detection by only short term measurement.

Figure 5:
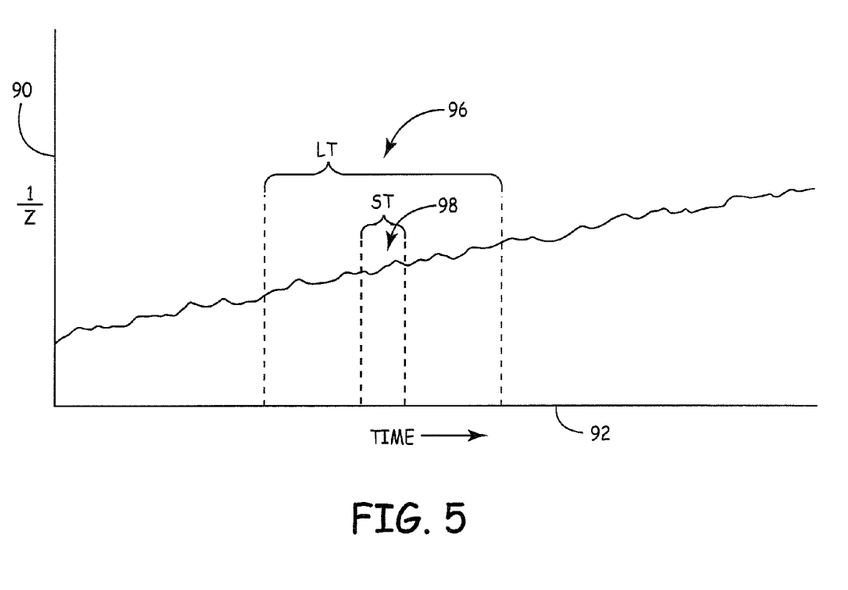
FIG. 5 is a graph of the FIG. 1 device operation in terms of the reciprocal of impedance over time.

FIG. 5 is a graph of the device 18 operation using the exemplary detection algorithm represented by the flow chart of FIG. 4. The vertical axis 90 is resistance, the reciprocal of impedance (1/Z). Therefore, the greater the lung congestion (i.e., the larger the fluid volume in the patient's lungs), the higher the impedance or the lower the resistance. The horizontal axis 92 represents time. The long-term average of the impedance measurement has a characteristic value that filters out the short-term variations of the measurement. In the Figure, the LT value 96 of curve or slope 94 exhibits a more gradual slope than the ST value 98. The difference between the two is used to determine whether an alarm condition is occurring (LT−ST=V≥threshold).

In addition to the baseline impedance, impedance measurements at the frequency of 128 Hz can detect impedance changes with every pumping cycle, to provide indirect information on stroke volume, heart rate, and cardiac output calculated therefrom. Additionally, by adequate low pass filtering, the indirect tidal volume of ventilation can be separated out, as well as respiratory rate. This is done by conventional signal processing techniques such as zero crossing and peak level detecting either in analog or digital format, or a combination of both, as the low power consumption requirements of an implantable device mandate. Examples of these techniques are described, for example, in Alt patents U.S. Pat. Nos. 5,014,703, 5,014,700, 5,031,615, 4,884,576, and 5,003,976. Typically, ventilation is in a range from 0.2 Hz to 0.8 Hz, while cardiac events are in a range from 1 Hz to 3 Hz. Both subsignals, cardiac and ventilation, can be used in addition to determine congestive heart failure indicated by decrease in stroke volume, relative decrease in tidal volume, increase in heart rate, and increase in ventilation rate.

A power saving can be achieved in the device by limiting the impedance measurement to fixed periods separated by intervals of no measurement, or even sporadic measurements, rather than performing continuous impedance measurements.

The impedance measurement electrodes are used in the device of the present invention to monitor the patient's EKG, as well as to obtain the raw data necessary for calculating absolute impedance, ventilation, and long- and short-term averages of impedance and ventilation. Also, the cardiac- and ventilation-derived impedance phenomena are correlated to the EKG for better evaluation of the cardio-pulmonary status of the patient.

The location where measurements are taken is of similar importance to the manner of taking the measurements. For example, the spacing between the measurement electrodes 14, 16 determines the volume and area of measurement. By spacing these electrodes at least 4 cm apart, the depth of measurement is increased beyond only the tissue in the immediate vicinity of the electrode, to the tissue for which specific impedance and impedance changes are sought to be measured, typically to a depth of up to 10 cm of lung tissue. Also, performing the measurements on the patient's left side rather than the right side, and particularly on the anterior lateral lower left thorax, enables early detection of changes in left ventricular parameters and congestion in the lung circulatory system, rather than limiting the measurement to tissue and liver impedance which is primarily a function of congestion of the right heart. Additionally, at this preferred location for conducting the measurements, the cardiac phenomena and stroke volume dependent impedance changes are more easily detected than on the right side or the upper left thorax where impedance changes primarily follow blood circulation.

The present invention provides additional features and operating functions to the basic device 18, as described below.

The electrodes used in device 18 to determine the impedance of the lungs are also used to measure the patient's EKG, and may also be used to provide other information. Here, the EKG information can be stored and evaluated in a conventional loop recorder, encompassed by the depiction of memory 44 of the block diagram shown in FIG. 3. A loop recorder serves to record trends of bradycardia and tachycardia, and also to provide morphology as well as rate information. The memory detects abnormal EKGs in a first in, first out method, so that a part of the EKG is always present and stored according to state of the art techniques.

The device of the present invention also incorporates a mechano-electrical converter 102 (illustrated by the dashed block in FIG. 3), such as an accelerometer or a piezoelectric crystal bound to the case. The information derived from the mechanical-electrical converter enables a reasonably accurate indication of patient activity to be derived. The quotient mentioned earlier herein for heart rate and activity provides a measure of the cardio-pulmonary status of the patient. In addition to the two parameters of EKG information and heart rate/activity, a local impedance value is obtained and correlated to the previous ones as an additional parameter for evaluating the cardio-pulmonary status of the patient.

This means that under normal conditions of everyday life, for a given average activity of the patient indicated by a certain activity signal level, a certain heart rate and ventilation signal is typical for a patient in a compensated and sufficient cardio-pulmonary status. As the cardiac function deteriorates over time due to the patient's underlying congestive heart failure problems, the ventilation and/or heart rate becomes relatively high for the same amount of physical activity detected from the accelerometer signal. This can be evaluated by analyzing the quotient of activity to ventilation or activity to heart rate and ventilation. Also, the decrease or absence of physical activity in light of impedance derived indication of congestion is another confirmation of the occurrence of congestive heart failure.

Suitable accelerometers are described in the prior art, such as the aforementioned Alt patent U.S. Pat. No. 5,014,703. As further described in the '703 patent, the accelerometer may be integrated into hybrid electronic circuitry and mounted on the same substrate as other electronic components such as capacitors, resistors and microprocessors. The most accurate technique for detecting patient activity with such an accelerometer is to measure the acceleration and deceleration in the horizontal axis. Accordingly, the integration into the hybrid circuit is preferably in the horizontal direction, since the highest sensitivity and truest activity signal is obtained in this measurement direction that makes the implant direction of the device less critical.

The subcutaneous impedance measurement from an electrode set incorporating at least two electrodes—in this case, the excitation and measurement—occurs at the same electrodes or preferably more than two electrodes, e.g., four electrodes, to provide a more stable signal Additionally, more than two electrodes enables the derivation of a clear EKG signal through the same electrodes on the case.

Figure 6:
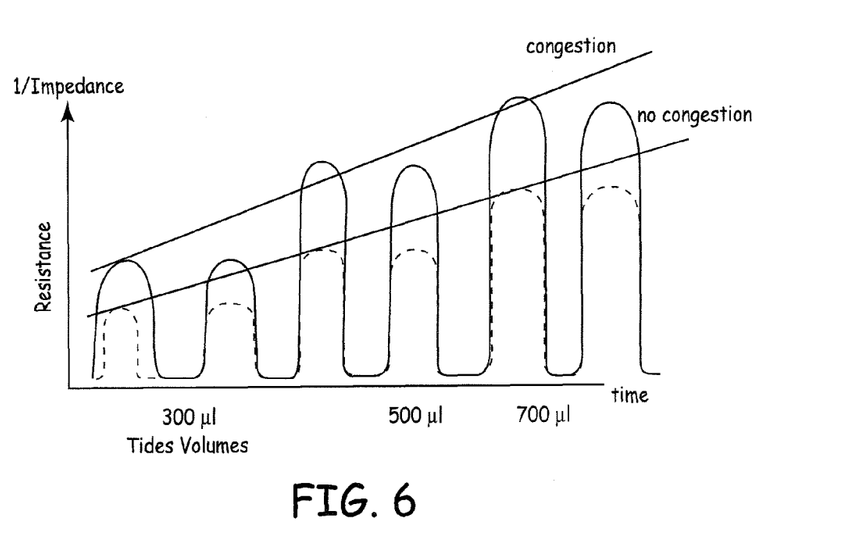
FIG. 6 is a graph illustrating the correlation between impedance and tidal volume with time detected or measured by the device of the present invention for a fictitious CHF patient.

As shown in the graph of FIG. 6, the impedance signal not only detects the ventilation rate from a subcutaneous location, but can also detect the ventilation depths, i.e., tidal volume with a linear correlation. Applicant has shown through many experiments that the correlation between ventilation rate or respiratory rate detected from such a subcutaneous impedance measurement and true respiratory rate is $r^2=0.99$, where r is the correlation coefficient; and also, a high correlation exists between the impedance signal amplitude and the tidal volume, i.e., the amount of air ventilated and the amplitude of the impedance signal. This correlation is also illustrated in FIG. 6. Therefore, it is feasible to measure ventilation, which is the product of respiration rate and respiration depth, or in other words, tidal volume, with high accuracy by subcutaneous impedance. Interestingly, this ventilation measurement has a linear correlation with true ventilation.

An additional finding of interest is that with increasing congestion of the lungs, the absolute amplitude of such a signal increases for the same amount of air ventilated. This is attributable to the fact that as the difference between inspiration and expiration becomes more pronounced, the lung congestion is greater, as is the effect of air in the lungs with inspiration and expiration in determining the amplitude changes.

Accordingly, the observation of a reduced product between respiratory rate and tidal volume amplitude has interesting implications, both for the detection of congestive heart failure, and also for the rate control of an implanted cardiac pacemaker, whose rate is determined by ventilation detected from a subcutaneous location. Additionally, the accelerometer in the device is used as a second sensor for rate control.

The signal processing performed to detect ventilation is conventional, using standard signal processing techniques such as peak level detection, zero crossing, and the like. Aside from amplitude, the integral of the ventilation signal curve also can be applied by the same means (FIG. 6), in which the simplest and least energy-consuming means are the most preferable. Ventilation volume over time measured in this way is the product of ventilation amplitude and respiratory or ventilation rate. If this product is above a certain predetermined minimum level, indicating either that the respiratory rate and tidal volume product is increasing, or that relative increases are occurring because the patient is becoming continuously congested, then an alarm or monitoring function can be activated and either transmitted by conventional telemetry to an external device (e.g., a programmer) or by triggering an alarm function in the device itself, to alert the patient or a care giver.

The evaluation of the ventilation and of baseline DC impedance is done in the way described previously herein, by running independent long and short term averages for the respective signals and comparing long and short term values to each other. A certain threshold deviation indicates congestion. In addition, more complex algorithms involve the comparison of physical activity and impedance/ventilation/heart rate both as actual values and as short and long term averages to each other, and the quotient of cardio-pulmonary signals to physical activity is indicative of congestion.

Figure 7:
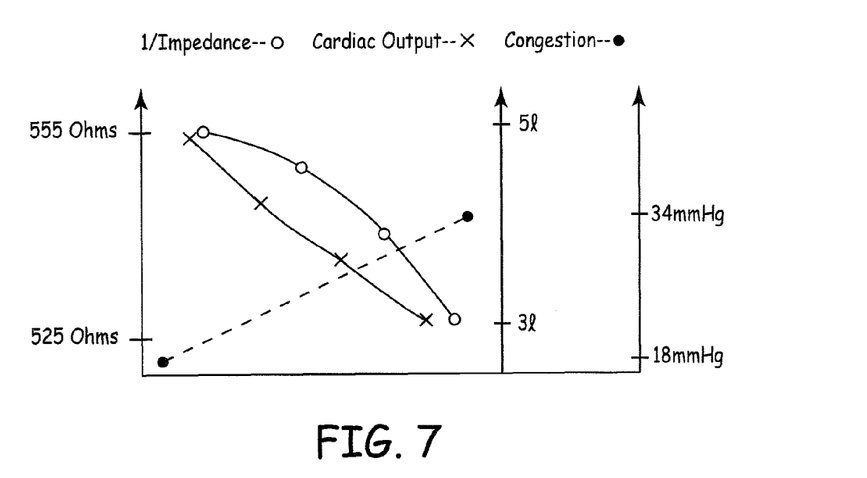
FIG. 7 is a graph illustrating the correlation between impedance, cardiac output and congestion as detected by a device of the present invention, for a fictitious patient.

The ventilation function can be monitored with a subcutaneous device, and ventilation is not only respiratory rate but also the amplitude representing the depth of respiration. DC amplitude also decreases with decreasing cardiac output and with increasing congestion. Experimental measurements obtained by the applicant demonstrate a roughly 20 to 30 ohm decrease in the subcutaneous impedance measurement with increasing congestion, and a linear correlation between a reduction in cardiac output and a reduction in impedance. Also, the experimental results indicate even an inverse correlation between an increase in end-diastolic pressure, represented by pulmonary capillary pressure or left atrial pressure, or diastolic left ventricular pressure and impedance. This correlation is illustrated in the graph of FIG. 7.

The device of FIG. 3 may be viewed as part of an implantable rate adaptive cardiac pacemaker constituting an improvement in which the electrodes situated on one of a housing, and a header of the pacemaker, and the electronic module 18 measures impedance changes at the electrodes to control the pacing rate generated by the pacemaker. Accelerometer 102 detects the status of physical activity of the patient to assist in adjusting the pacing rate of the pacemaker.

Although a presently contemplated best mode, preferred embodiments and methods of practicing the invention have been described in this specification, those skilled in the art will recognize from a consideration of the foregoing description that variations and modifications of the disclosed embodiments and methods may be made without departing from the spirit and scope of the invention. It is therefore intended that the invention shall be limited only to the extent required by the appended claims and the rules and principles of applicable law.

What is claimed is:

1. An implantable device-implemented method of early detection and monitoring of congestive heart failure in a patient, which comprises the steps of:
   measuring local impedance of a portion of the patient's body generally occupied by the lungs solely through surface mounted electrodes on the device with the device implanted subcutaneously in the patient's body,
   detecting when the local impedance measurements using said surface mounted electrodes are indicative of a condition of edema,
   detecting the patient's heart rate/activity pattern through said surface mounted electrodes while concurrently monitoring said local impedance measurements to evaluate cardiopulmonary status of the patient, and
   evaluating said congestive heart failure based on (1) said edema and (2) said cardiopulmonary status;
   wherein at least some of said surface mounted electrodes used in said measuring step are the same surface mounted electrodes used in said detecting the patient's heart rate/activity pattern step.

2. A method for evaluating congestive heart failure in a patient having a heart and lungs with a subcutaneous monitoring device having a plurality of surface-mounted electrodes implanted in a vicinity of said lungs, comprising the steps of:
   measuring an impedance value of said lungs and said vicinity of said lungs solely through at least some of said plurality of surface-mounted electrodes on the subcutaneous monitoring device;
   detecting an edema of said lungs and said vicinity of said lungs using said at least some of said plurality of surface-mounted electrodes;
   detecting a cardiopulmonary status of said patient using said at least some of said plurality of surface-mounted electrodes;
   evaluating said congestive heart failure as a function of said edema and said cardiopulmonary status;
   wherein at least some of said plurality of surface mounted electrodes used in said measuring step are the same plurality of electrodes used in said detecting an edema step and said detecting a cardiopulmonary status step.

3. A method as in claim 2 wherein said detecting edema step occurs concurrently with said detecting cardiopulmonary status step.

* * * * *